US012383356B2

(12) United States Patent
Iordachita et al.

(10) Patent No.: US 12,383,356 B2
(45) Date of Patent: Aug. 12, 2025

(54) BODY MOUNTABLE ROBOT

(71) Applicants: The Johns Hopkins University, Baltimore, MD (US); Children's National Medical Center, Washington, DC (US)

(72) Inventors: Iulian I. Iordachita, Lutherville, MD (US); Jin Seob Kim, Ellicott City, MD (US); David Levi, Baltimore, MD (US); Kevin Cleary, Potomac, MD (US); Reza Monfaredi, Rockville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 18/414,698

(22) Filed: Jan. 17, 2024

(65) Prior Publication Data

US 2024/0180644 A1      Jun. 6, 2024

Related U.S. Application Data

(62) Division of application No. 16/768,508, filed as application No. PCT/US2018/062450 on Nov. 26, 2018, now Pat. No. 11,911,123.

(Continued)

(51) Int. Cl.
*A61B 34/32* (2016.01)
*A61B 90/00* (2016.01)
(Continued)

(52) U.S. Cl.
CPC .............. *A61B 34/32* (2016.02); *A61B 90/11* (2016.02); *A61B 2017/3409* (2013.01); *A61B 2090/374* (2016.02)

(58) Field of Classification Search
CPC .............. A61B 90/11; A61B 2090/374; A61B 2090/3409; A61B 34/32
See application file for complete search history.

(56) References Cited

U.S. PATENT DOCUMENTS

| 4,522,811 A | 6/1985 | Eppstein et al. |
| 4,816,567 A | 3/1989 | Cabilly et al. |

(Continued)

FOREIGN PATENT DOCUMENTS

| KR | 20160148326 A | 12/2016 |
| WO | 2018232316 A1 | 12/2018 |

(Continued)

OTHER PUBLICATIONS

International Search Report and Written Opinion for Application No. PCT/US2018/62450, mailed on Apr. 16, 2019, 12 pages.

(Continued)

*Primary Examiner* — Chao Sheng
(74) *Attorney, Agent, or Firm* — Harrity & Harrity, LLP

(57) ABSTRACT

A body mountable robot may include a set of stages disposed in a parallel configuration. The body mountable robot may include a set of actuating joints, wherein an actuating joint, of the set of actuating joints, is configured to rotate with respect to a corresponding stage of the set of stages. The body mountable robot may include at least one actuator, wherein the at least one actuator is configured to actuate at least one actuating joint of the set of actuating joints. The body mountable robot may include a set of scissor mechanisms, wherein a scissor mechanism, of the set of scissor mechanisms, that is coupled to the actuating joint, is supported by the corresponding stage, and wherein the scissor mechanism is configured to translate with respect to the corresponding stage.

20 Claims, 12 Drawing Sheets

Related U.S. Application Data

(60) Provisional application No. 62/592,467, filed on Nov. 30, 2017.

(51) Int. Cl.
  *A61B 90/11* (2016.01)
  *A61B 17/34* (2006.01)

(56) References Cited

U.S. PATENT DOCUMENTS

| | | | |
|---|---|---|---|
| 5,641,870 | A | 6/1997 | Rinderknecht et al. |
| 6,468,798 | B1 | 10/2002 | Debs et al. |
| 7,881,823 | B2 | 2/2011 | Demathelin et al. |
| 2005/0250220 | A1 | 11/2005 | Kozulic |
| 2012/0143029 | A1 | 6/2012 | Silverstein et al. |
| 2014/0275979 | A1 | 9/2014 | Fujimoto et al. |
| 2014/0371584 | A1 | 12/2014 | Cleary et al. |
| 2015/0118740 | A1 | 4/2015 | Wang et al. |
| 2020/0173985 | A1 | 6/2020 | Dong et al. |
| 2021/0032213 | A1 | 2/2021 | Yeager et al. |
| 2022/0117684 | A1 | 4/2022 | Iordachita et al. |

FOREIGN PATENT DOCUMENTS

| | | | |
|---|---|---|---|
| WO | 2019213096 | A1 | 11/2019 |
| WO | 2020198537 | A1 | 10/2020 |
| WO | 2022079245 | A1 | 4/2022 |

OTHER PUBLICATIONS

Choithia C., et al., "Canonical Structures for the Hypervariable Regions of Immunoglobulins," Journal of Molecular Biology, 1987, vol. 196, pp. 901-917.

Clackson T., et al., "Making Antibody Fragments using Phage Display Libraries," Nature, 1991, vol. 352, pp. 624-628.

Davies D.R., et al., "Antibody-antigen Complexes," Annual Review of Biochemistry, 1990, vol. 59, pp. 439-473.

Honegger A., et al., "Yet Another Numbering Scheme for Immunoglobulin Variable Domains: An Automatic Modeling and Analysis Tool," Journal of Molecular Biology, 2001, vol. 309, pp. 657-670.

Jones P.T., et al., "Replacing the Complementarity-determining Regions in a Human Antibody with Those from a Mouse," Nature, 1986, vol. 321, pp. 522-525.

Kohler G., et al., "Continuous Cultures of Fused Cells Secreting Antibody of Predefined Specificity," Nature, 1975, vol. 256, pp. 495-497.

Kunz M, "Oncogenes in Melanoma: An Update," European Journal of Cell Biology, 2014, vol. 93, pp. 1-10.

Lee C., et al., "Tumor Metastasis to Lymph Nodes Requires YAP-dependent Metabolic Adaptation," Science, 2019, vol. 363, pp. 644-649.

Lefranc M.P., et al., "IMGT, The International ImMunoGeneTics database," Nucleic Acids Research, 1999, vol. 27, pp. 209-212.

Lorusso P.M., et al., "Targeted Therapy and Immunotherapy: Emerging Biomarkers in Metastatic Melanoma," Pigment Cell and Melanoma Research, 2020, vol. 33, pp. 390-402.

Malmqvist M., "Biospecific Interaction Analysis using Biosensor Technology," Nature, 1993, vol. 361, pp. 186-187.

Marks J.D., et al., "By-passing Immunization. Human Antibodies from V-gene Libraries Displayed on Phage," Journal of Molecular Biology, 1991, vol. 222(3), pp. 581-597.

Meixiong J., et al., "MRGPRX4 is a G protein-coupled Receptor Activated by Bile Acids that May Contribute to Cholestatic Pruritus," Proceedings of the National Academy of Sciences of the United States of America, 2019, vol. 116, pp. 10525-10530.

Morrison S.L., et al., "Chimeric Human Antibody Molecules: Mouse Antigen-binding Domains with Human Constant Region Domains," Proceedings of the National Academy of Sciences of the United States of America, 1984, vol. 81, pp. 6851-6855.

Patton E.E., et al., "Melanoma Models for the Next Generation of Therapies," Cancer Cell, 2021, vol. 39, pp. 610-631.

Presta L.G., "Antibody Engineering," Current Opinion in Biotechnology, 1992, vol. 2, pp. 593-596.

Riechmann L., et al., "Reshaping Human Antibodies for Therapy," Nature, 1988, vol. 332, pp. 323-327.

Ruiz M., et al., "IMGT, The International ImMunoGeneTics database," Nucleic Acids Research, 2000, vol. 28, pp. 219-221.

Scatchard G., "The Attractions of Proteins for Small Molecules and Ions," Annals of the New York Academy of Sciences, 1949, vol. 51, pp. 660-672.

Sun J., et al., "Principles of Targeted Therapy for Melanoma," The Surgical Clinics of North America, 2020, vol. 100, pp. 175-188.

Yu H., et al., "MRGPRX4 is a Bile Acid Receptor for Human Cholestatic Itch," Elife, 2019, vol. 8, pp. e48431.

Zapata G., et al., "Engineering Linear F(ab')2 Fragments for Efficient Production in *Escherichia coli* and Enhanced Antiproliferative Activity," Protein Engineering, 1995, vol. 8, pp. 1057-1062.

300

BODY MOUNTABLE ROBOT

RELATED APPLICATION(S)

This application is a divisional of U.S. patent application Ser. No. 16/768,508, filed May 29, 2020, which is a national stage entry of International Patent Application No. PCT/US2018/062450, filed Nov. 26, 2018, which claims priority under 35 U.S.C. § 119 to U.S. Provisional Patent Application No. 62/592,467, filed on Nov. 30, 2017, the contents of which are incorporated herein by reference in their entireties.

GOVERNMENT LICENSE RIGHTS

This invention was made with U.S. Government support under grant EB020003, awarded by the National Institutes of Health. The U.S. Government has certain rights in the invention.

BACKGROUND

Interventional magnetic resonance imaging (MRI) combines multiplanar cross-sectional imaging capabilities with soft tissue contrast. MRI guidance may be used for biopsy, drainage, percutaneous therapies, and many other clinical indications. Advances in MRI-compatible instruments have markedly increased the possibilities and practicability of interventional MRI. High contrast resolution of MRI makes interventional MRI useful for lesions that may be difficult to visualize with other modalities. Interventional MRI has an advantage of providing anatomic detail without subjecting the clinician or patient to ionizing radiation, which may be especially important in pediatrics.

As an example, arthrography is the evaluation of joint condition using imaging, such as computed tomography (CT) and MRI. To perform arthrography, contrast is injected in a joint of a patient, and a contrast spread is evaluated using imaging. From the imaging, a radiologist may diagnose suspected derangement of articular labral structures, cartilage, and congenital joint dysplasias in the patient. In comparison to other radiological imaging modalities, MRI offers improved soft-tissue contrast, which is especially useful in shoulder arthrography where there exists many layers of soft tissue and bone. Some magnetic resonance (MR) arthrography procedures involve the injection of a contrast solution guided by fluoroscopy. This may be followed by an MR image of a joint space for suspected issues. Such a two-step procedure may result in anxiety for the patient, longer sedation times (e.g., which may be particularly difficult for younger patients), radiation exposure from fluoroscopic imaging, and increased healthcare cost due to the use of both the fluoroscopy and MRI suites.

SUMMARY

According to some possible implementations, a body mountable robot may include a set of stages disposed in a parallel configuration. The body mountable robot may include a set of actuating joints, wherein an actuating joint, of the set of actuating joints, is configured to rotate with respect to a corresponding stage of the set of stages. The body mountable robot may include at least one actuator, wherein the at least one actuator is configured to actuate at least one actuating joint of the set of actuating joints. The body mountable robot may include a set of scissor mechanisms, wherein a scissor mechanism, of the set of scissor mechanisms, that is coupled to the actuating joint, is supported by the corresponding stage, and wherein the scissor mechanism is configured to translate with respect to the corresponding stage.

According to some possible implementations, a system may include a body mountable robot configured for use within an MRI machine. The body mountable robot may include a set of stages disposed in a parallel configuration. The body mountable robot may include a set of actuating joints. The body mountable robot may include at least one actuator. The body mountable robot may include a set of scissor mechanisms. The body mountable robot may include a needle guide. The body mountable robot may include a robot control system to control the body mountable robot to move the needle guide with regard to four degrees of freedom of movement. The system may include a control device to transmit control signals to the robot control system based on imaging information from the MRI machine.

According to some possible implementations, a control device may determine to position a needle guide, wherein the needle guide is supported by an upper stage and a lower stage of a body mountable robot, wherein the upper stage includes a first actuating joint to move about the upper stage, a first actuator to move the first actuating joint, and a first scissor mechanism to move about the upper stage, wherein the lower stage includes a second actuating joint to move about the lower stage, a second actuator to move the second actuating joint, and a second scissor mechanism to move about the lower stage. The control device may determine a set of commands for the first actuator or the second actuator to position the needle guide. The control device may transmit the set of commands to a robot control system of the body mountable robot to cause the first actuator or the second actuator to move at least one of the first actuating joint, the first scissor mechanism, the second actuating joint, or the second scissor mechanism to reposition the needle guide.

DETAILED DESCRIPTION

Figure 1A:
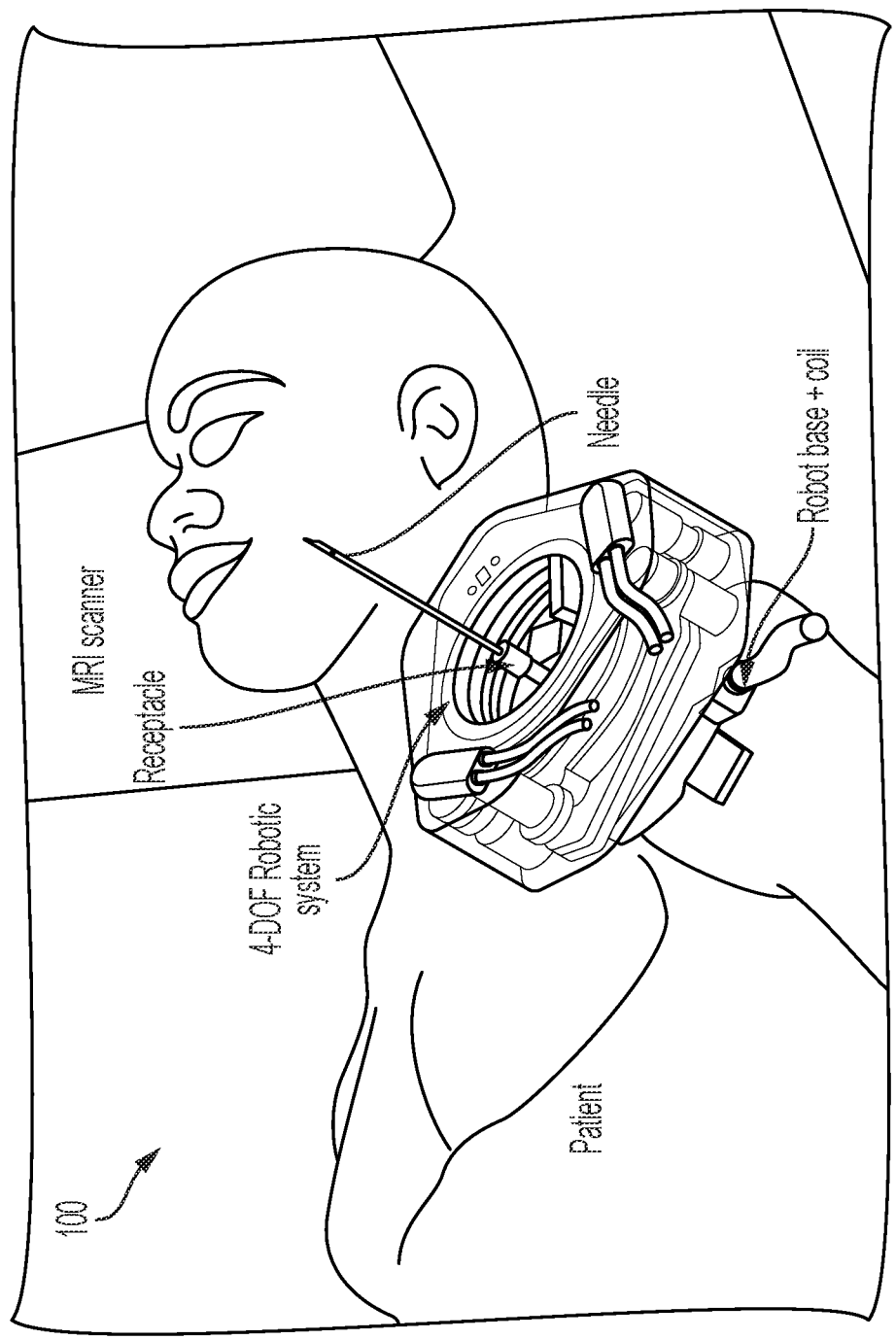
FIGS. 1A-1D are diagrams of example implementations described herein.

The following detailed description of example implementations refers to the accompanying drawings. The same reference numbers in different drawings may identify the same or similar elements.

Some magnetic resonance (MR) based modalities for performing arthrography result in various detriments to a patient. For example, contrast solution may be injected into a patient before MR imaging is performed using an MRI machine. Thereafter, a surgical procedure may be performed based on the previous MR imaging. When a patient moves, it may be difficult for a surgeon or other technician to effectively use the imaging to guide a surgical procedure. For example, when using a surgical robotics device, movement of the patient may cause the surgical robotics device to become misaligned with the patient relative to the imaging.

Some implementations described herein provide a four-degree-of-freedom parallel robot for MRI guided percutaneous interventions. The robot may include two parallel circular stages along which two actuating joints may move to guide a needle for a surgical intervention. In some implementations, the robot may be patient mounted. In this way, the robot, which may be termed a body mountable or body mounted robot, may maintain alignment to the patient even after the patient moves. Moreover, based on the circular stage configuration, the robot may provide improved rigidity and reduced inertial effects relative to other surgical robotics devices, as described herein. Moreover, some implementations described herein may have a reduced quantity of moving components relative to other surgical robotics devices, which may enhance safety during operation of the robot, reduces a likelihood of breakage, and/or the like.

Some implementations described herein provide a 4-degree-of-freedom (DOF) robot using a parallel architecture system for orienting and positioning a needle guide (e.g., a receptacle to receive a needle for a surgical intervention). Although a shoulder mounted robot is described herein, other mounting configurations are possible. For example, the robot may be securely mounted on another part of the patient to enabling imaging and surgical intervention at another part of the patient. In this case, the robot may be used for lumbar transforaminal epidural injections, piriformis muscle injection, pudendal nerve injection, sacroilliac joint injection, pars interaricularis defect intervention for a lumbar spine, pelvic and sacral nerve injections, and/or the like. In some implementations, the robot may be used in arthrography procedures or for other types of procedure. In some implementations, the robot may provide needle angulation in range of approximately plus or minus 30° with regard to a reference position. In some implementations, the robot may be associated with a circular workspace with an approximately 10 centimeters (cm) diameter. In some implementations, materials of the robot may be MRI-compatible (e.g., non-magnetic or minimally magnetic).

In some implementations, the robot may be associated with dimensions in a horizontal plane (e.g., a plane of a circular stage) of less than approximately 20 cm to fit patient shoulder anatomy. In some implementations, a thickness of the robot at a needle guide section may be less than approximately 5 cm to reduce the unused length of the needle. In some implementations, the robot may include an actuation mechanism, such as an MRI-compatible piezoelectric motor, an MRI-compatible encoder, and/or the like. In some implementations, the robot may include inputs and/or outputs to enable compatibility with a robot control system described herein as well as with other robot control systems.

FIGS. 1A-1D are diagrams of an example implementation 100 described herein. FIG. 1A-1D show an example of a shoulder-mounted, parallel-platform robot described herein.

As shown in FIG. 1A, the robot, which may be a 4-DOF robotic system, as described herein, is attached on a patient's shoulder. In this case, the patient may be disposed in an MRI scanner to enable concurrent MRI imaging and surgical intervention.

Figure 1B:
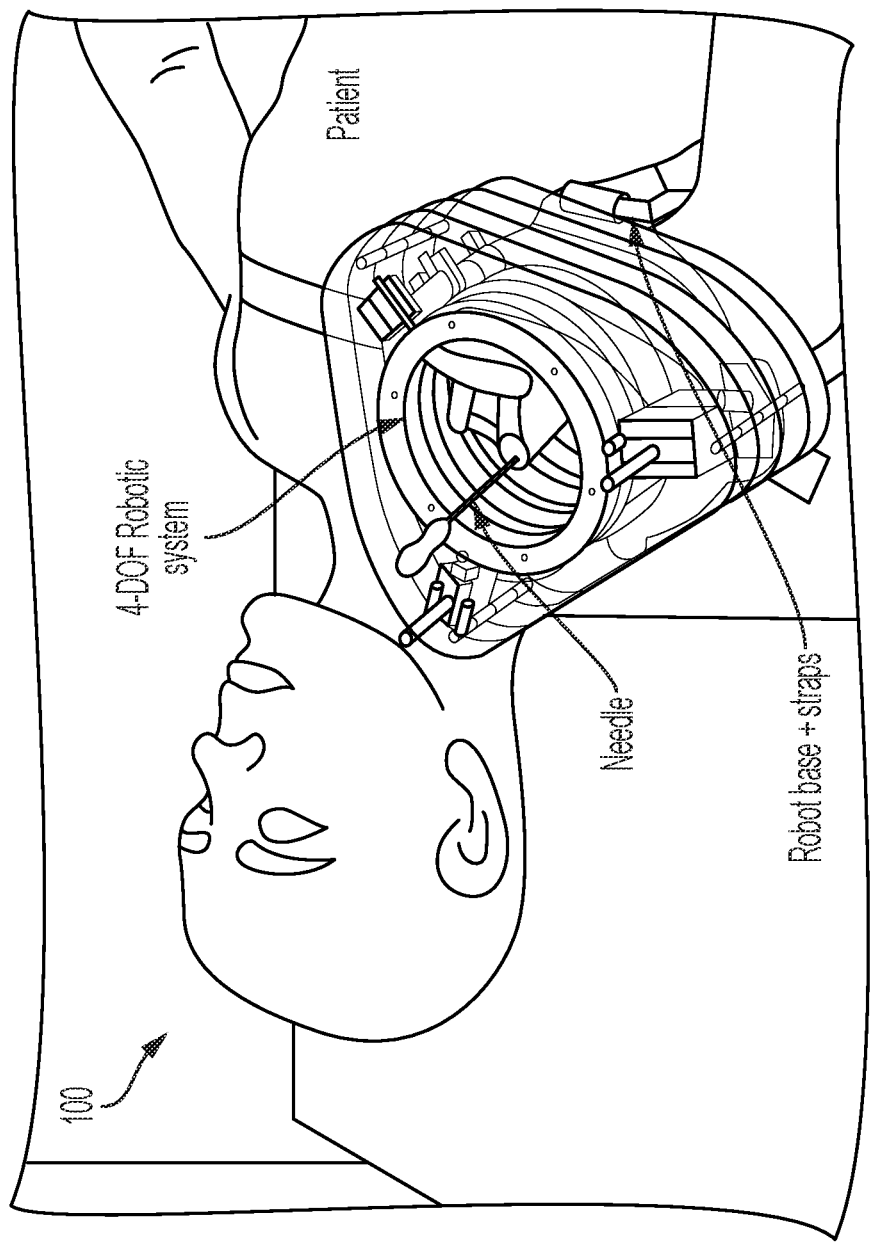

As shown in FIG. 1B, the robot may be attached to a shoulder of a mannequin. In this case, the robot may be attached using straps to securely maintain a base of the robot in position on the shoulder of the mannequin. In some implementations, the robot of FIG. 1B is approximately 22.5 cm by 22.5 cm by 6 cm. The parallel-platforms of the robot are shown in FIGS. 1A and 1B, and form a set of stages to provide the 4-DOF for the robot (e.g., for manipulating a position of a receptacle and the needle disposed therein with respect to a patient). For example, each stage may provide 2-DOF for the robot, and may combine to provide 4-DOF for the robot. The parallel-platforms sit above a region-of-interest (e.g., the shoulder). The parallel-platforms of the robot are disposed on the shoulder and are attached with the straps to make sure that the robot is securely held at the region-of-interest despite movement of the patient. In this way, the robot maintains an orientation with respect to a patient, thereby improving surgical interventions relative to other surgical robotics devices. Other attachment mechanisms may be possible. A needle is shown in FIGS. 1A and 1B and movement of the needle is effectuated by the 4-DOF robot. In addition to straps, the robot may also include a base to allow for the robot to be positioned at the region-of-interest.

As an example of a surgical procedure using the robot, a patient may be positioned on an MRI platform, the robot may be secured to the patient (e.g., using the straps), the MRI may scan a region of interest, a control device (described herein), may determine a trajectory for a needle controlled by the robot, the control device may register the robot with images from the MRI scan (e.g., the control device may correlate a position of the robot with imaging data), the control device may cause the robot to insert a needle, the control device may cause the needle to inject contrast or medication, and the control device may cause follow up imaging to be performed using the MRI. In this way, by enabling use of the robot in situ with an imaging device (e.g., the MRI), a quantity of steps may be reduced relative to another technique where the patient must be moved from an imaging device to have a surgical robotics intervention performed, and then returned to the imaging device. In some implementations, the robot may include an MRI imaging coil integrated into the robot. In this way, imaging may be performed concurrent with robotic surgical intervention, thereby enabling robotic assistance for contrast injection, medication injection, and/or the like. Moreover, based on integrating an MRI imaging coil into the robot, the MRI imaging coil may be positioned as close to a patient as possible, which may improve imaging sensitivity.

Figure 1C:
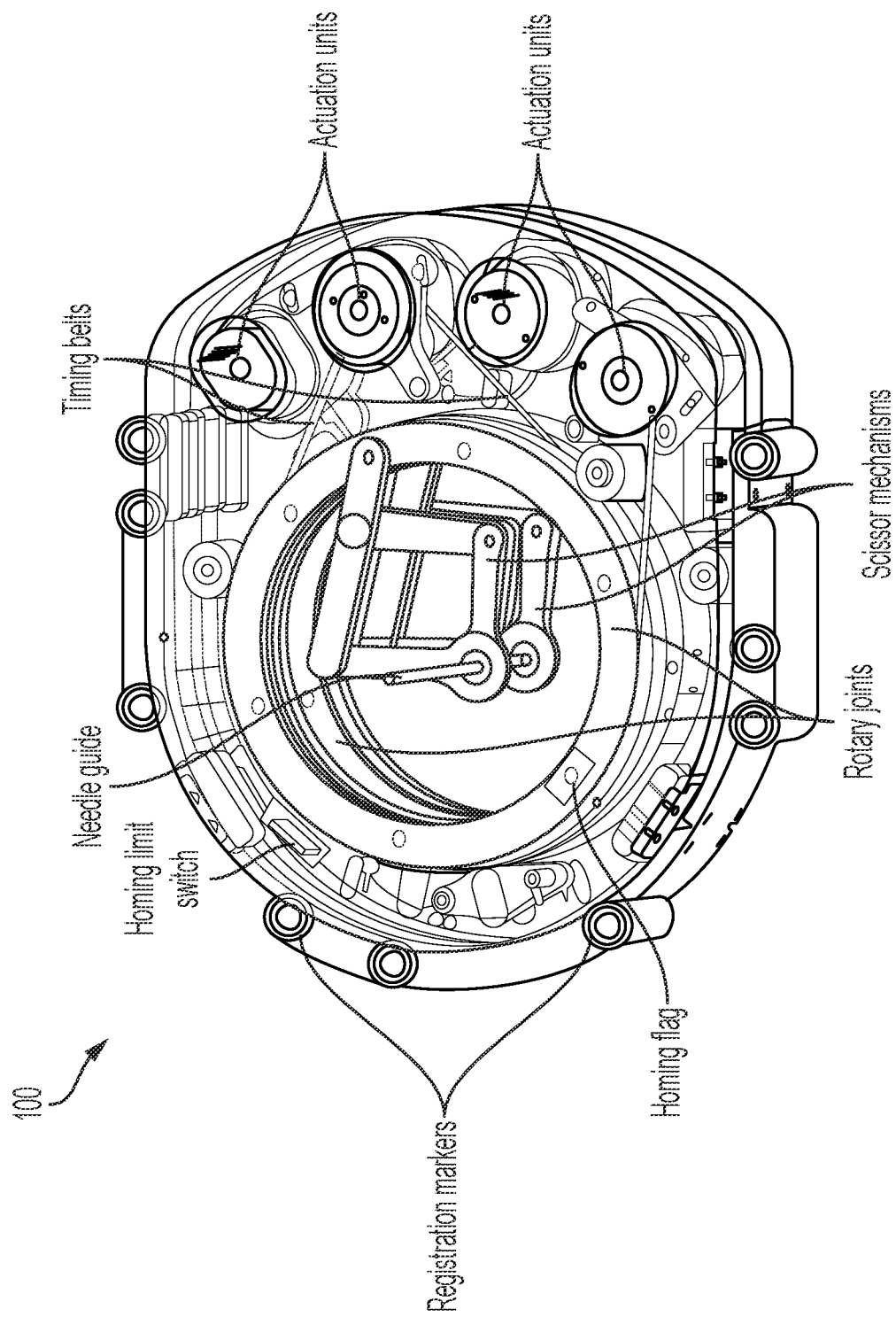

As shown in FIG. 1C, the robot may include a set of scissor mechanisms, a set of rotary joints, a set of actuation units (e.g., actuators), a set of timing belts (e.g., to actuate the robot based on movement of the actuation units), a set of registration markers, a homing flag, a homing limit switch, and/or the like. In some implementations, the registration markers may be visible to MRI imaging to enable a technician or a control device to locate the robot relative to a patient. In some implementations, the homing flag and homing limit switch may be used to determine a position of a needle supported by the robot, thereby enabling control commands to be determined (e.g., by a control device) to move the needle from an initial position to a target position.

Figure 1D:
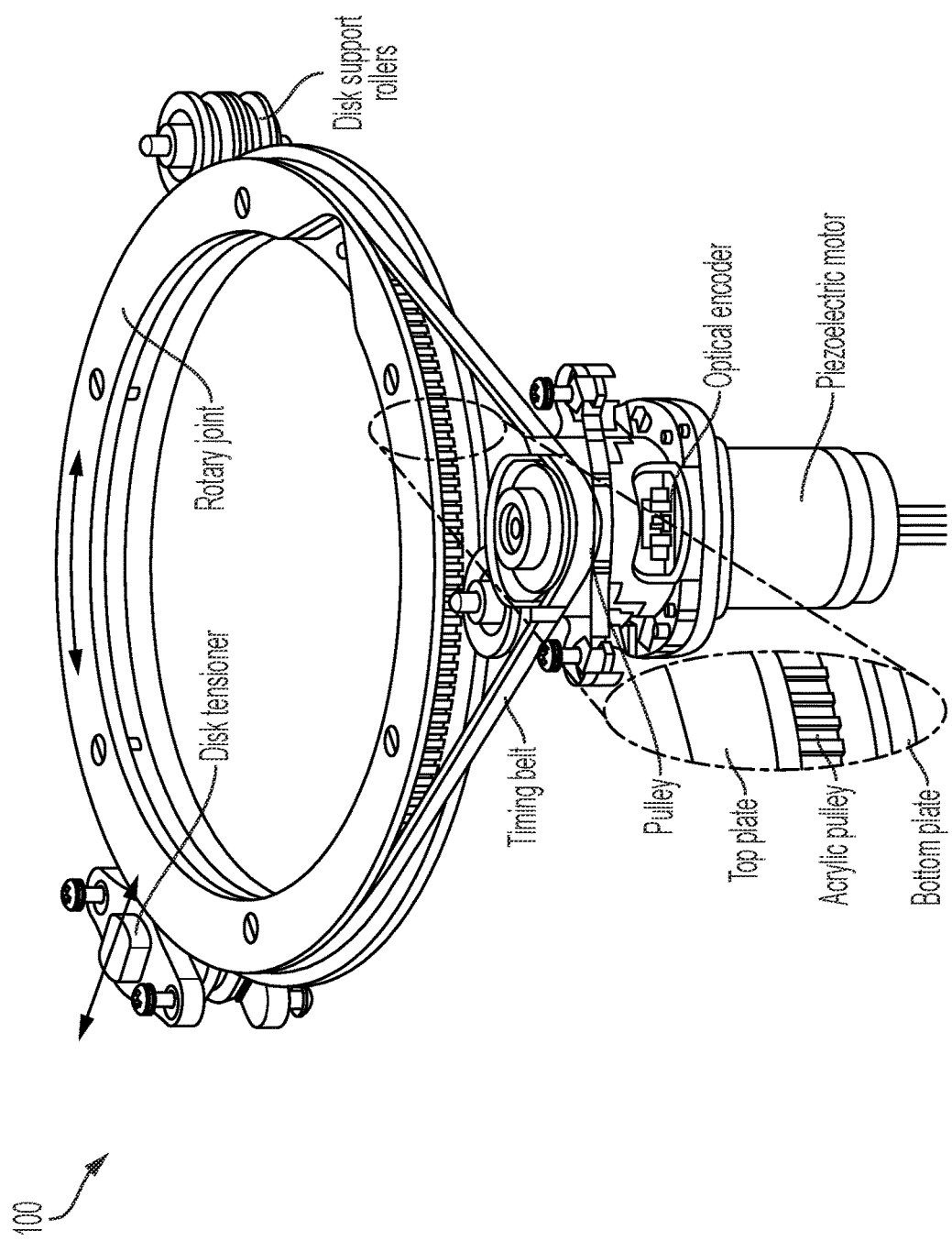

As shown in FIG. 1D, the actuation unit may include a piezoelectric motor, an optical encoder, and a pulley to support the timing belt. The timing belt may couple to disk support rollers on a stage of the robot. The stage of the robot may include a top plate and a bottom plate with a groove between the top plate and the bottom plate to receive the timing belt. A disk tensioner may be coupled to the stage of the robot to enable tensioning of the timing belt. In this way, the actuation unit can effectuate movement of a needle relative to the stage (e.g., relative to the robot) to enable robotic surgical intervention.

As indicated above, FIGS. 1A-1D are provided merely as an example. Other examples may differ from what was described with regard to FIGS. 1A-1D.

Figure 2:
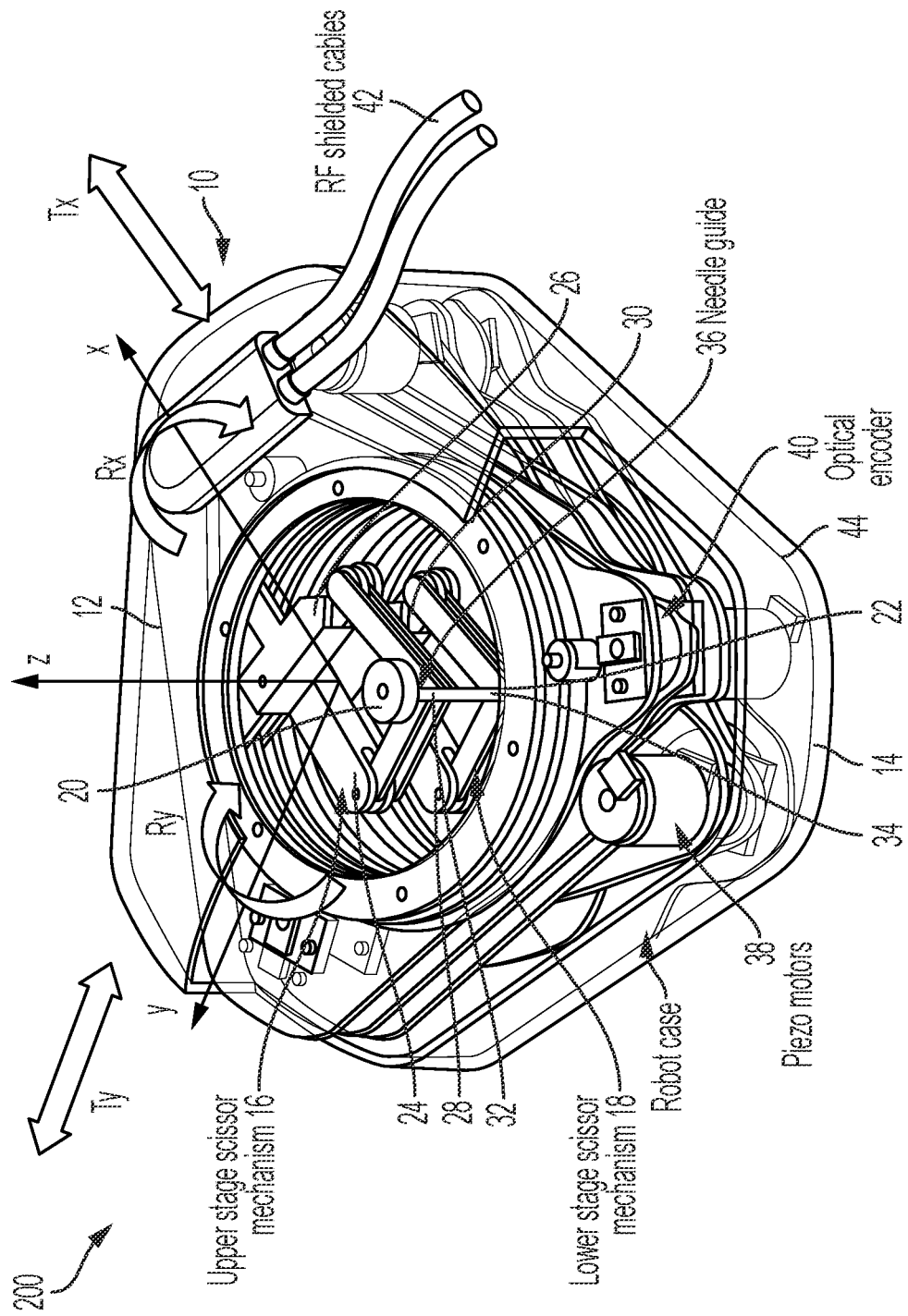
FIG. 2 is a diagram of an example implementation described herein.

FIG. 2 is a diagram of an example implementation 200 described herein. FIG. 2 shows a parallel-platform, MRI-compatible robot 10, described herein.

Robot 10 may include a sandwich configuration of two circular stages. For example, robot 10 may include an upper (superior) stage 12 and a lower (inferior) stage 14. Each stage 12/14 supports a corresponding scissor mechanism 16/18. Each of the two stages 12 and 14 includes two discs 20/22 rotating about a vertical axis. Each disc 20/22 may be connected to two link bars. For example, disc 20 may be connected to link bars 24 and 26 and disk 22 may be connected to link bars 28 and 30. Link bars 24/26/28/30 may form arms of scissor mechanisms 16/18. Two outer link bars of each stage are connected at the ends by a spherical joint 32 and 34, respectively, through which the needle guide 36 passes. Needle guide 36 may be a receptacle for a needle for a surgical intervention. Spherical joints 32/34 may be end effectors of respective circular stages. For example, needle guide 36 may be fixed to an actuating joint of inferior stage 14 and may translate through an actuating joint of superior stage 12. Each spherical joint 32, 34 may be a stage end-effector, and may have 2-DOF. Thus, stages 12/14 with corresponding spherical joints 32/34 may provide 4-DOF for needle guide 36. For example, stages 12/14 may provide translation motion with regard to the y-axis (Ty), translational motion with regard to the x-axis (Tx), rotational motion with regard to the y-axis (Ry), and rotational motion with regard to the x axis (Rx). Further, based on a needle being insertable via needle guide 36, a further degree of freedom may be translational with regard to the z-axis.

As further shown in FIG. 2, robot 10, which may be an MRI-compatible robot comprised of MRI-compatible materials, may include actuator. The actuator may be at least one piezoelectric motor 38, which may be termed a piezo-motor, and may be associated with an optical encoder 40. In some implementations, robot 10 may include a pair of piezoelectric motors 38 corresponding to each one of the actuating joints. In some implementations, robot 10 may include a total of four piezoelectric motors 38. In some implementations, robot 10 may include a pair of optical encoders 40 for each of the actuating joints. For example, robot 10 may include four optical encoders. RF-shielded cables 42 may provide power and a data connection for robot 10 (e.g., for a robot control system of the robot 10 to communicate with a control device, as described herein). In some implementations, robot 10 may include a housing 44. Components of the robot 10 may be made from MRI-compatible materials. In some implementations, robot 10 may include imaging markers to enable correlation of a position of robot 10 with imaging performed of a patient. For example, robot 10 may include a marker that is visible in MRI imaging, to enable location determination of a position of robot 10 in MRI imaging performed of a patient.

In this way, robot 10 may be associated with increased rigidity and decreased inertia for the component parts in motion. Moreover, by having the motors and encoders connected at a base, as illustrated in FIG. 2, accompanying cables may be fixed and may cause less physical interference between the moving components and a sterile plastic drape, thereby reducing a difficulty of performing a surgical intervention. Moreover, by reducing a quantity of relatively heavy parts in motion, robot 10 may achieve a stable center of mass, thereby achieving improved positioning accuracy. For example, by providing a sandwich configuration (e.g., a parallel-platform) mechanism, an issue of summing errors in serial robots is reduced.

In some implementations, robot 10 may be associated with dimensions of approximately 20 cm (x-axis) by 20 cm (y-axis) by 6 cm (z-axis). In some implementations, robot 10 may be associated with dimensions of approximately 18 cm by 18 cm by 5 cm.

As indicated above, FIG. 2 is provided merely as an example. Other examples may differ from what was described with regard to FIG. 2.

Figure 3A:
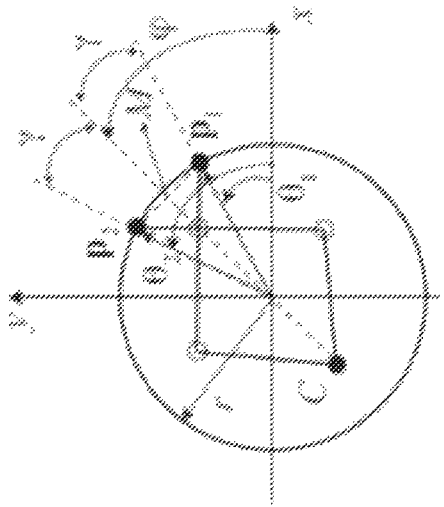
FIGS. 3A and 3B are diagrams of an example implementation described herein.
Figure 3B:
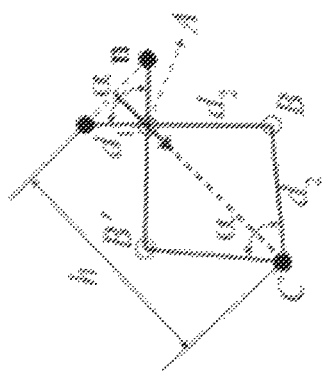

FIGS. 3A and 3B are diagrams of an example implementation 300 described herein. FIGS. 3A and 3B illustrate a representation of a circular stage, of multiple stages, of a robot described herein.

As described with regard to FIGS. 3A and 3B, a control device may receive an instruction to move a needle disposed in a receptacle of the robot. The control device may determine a set of commands to move the needle to enable surgical intervention using the needle. Although some implementations are described herein in terms of mathematical calculations to enable movement of the needle, the control device may use another technique, such as a lookup table of positions and/or the like.

As shown in FIG. 3A, a radius of the circular stage is represented r. Each stage, of the multiple stages, includes rigid links that are jointed (joints are denoted by circles in FIGS. 3A and 3B). For example, the points A, B, and B' (FIG. 3B) denote passive joints. Similarly, P1 and P2 (FIG. 3A) are points on the circular stage that are actuated to move along the circle. The point C denotes the position of the needle on this stage plane. The length of $\overline{P_1A}$ is equal to $\overline{P_2A}$, denoted as $d_1$. Also $\overline{AB}=\overline{AB'}=\overline{BC}=\overline{B'C}=d_2$. The control device may represent position vectors of P1 and P2, respectively, as:

$$p_1 = [r\cos\theta_1, r\sin\theta_1]^T, \qquad (1)$$

$$p_2 = [r\cos\theta_2, r\sin\theta_2]^T \qquad (2)$$

where $\theta_1$ and $\theta_2$ are joint variables representing angles of respective joints. Control device may determine that $0 \leq \theta_1 < \theta_2 \leq 2\pi$, and may determine:

$$p_2 p_1 = [r(\cos\theta_2 - \cos\theta_1), r(\sin\theta_2 - \sin\theta_1)]^T \qquad (3)$$

Control device may further determine an equilateral triangle of $\Delta P_1, P_2 A$ and by the law of cosines:

$$\alpha = \cos^{-1}\left(1 - \frac{\|p_2 - p_1\|^2}{2d_1^2}\right) = \cos^{-1}\left(1 - \frac{r^2}{d_1^2}(1 - \cos(\theta_2 - \theta_1))\right) \qquad (4)$$

In this case, because $\Delta ABC$ and $\Delta AB'C$ are equilateral, $\angle P_1 A P_2 = \angle BAB' = \angle BCB' = \alpha$. Thus, the control device may determine:

$$p_c = \frac{1}{2}(p_1 + p_2) + hn \qquad (5)$$

-continued where:

$$h = (d_1 + 2d_2)\cos\frac{\alpha}{2} \quad (6)$$

The control device may determine that there is a constraint that $\|p_2-p_1\|<2d_1<2r$. Based on the constraint, which means that n always points toward the center of the circle, the control device may determine the normal vector as $$n = R_z(90°)\frac{p_2 - p_1}{\|p_2 - p_1\|} = \frac{1}{\sqrt{2(1-\cos(\theta_2-\theta_1))}}\begin{pmatrix}-(\sin\theta_2 - \sin\theta_1)\\ \cos\theta_2 - \cos\theta_1\end{pmatrix} \quad (7)$$

where:

$$Rz(\theta) = \begin{pmatrix}\cos\theta & -\sin\theta\\ \sin\theta & \cos\theta\end{pmatrix} \quad (8)$$

which is equivalent to the rotation about the z-axis. Thus, based on $\theta_1$ and $\theta_2$, the control device may determine a position of the needle axis on each plane of the circular stage (e.g., an initial position, a target position, and/or the like). In this way, a control device may use equations 1-8 in translating an instruction to move a needle to a particular point to a set of commands to an actuator to cause the robot to position the needle.

As indicated above, FIGS. 3A and 3B are provided merely as an example. Other examples may differ from what was described with regard to FIGS. 3A and 3B.

Figure 4:
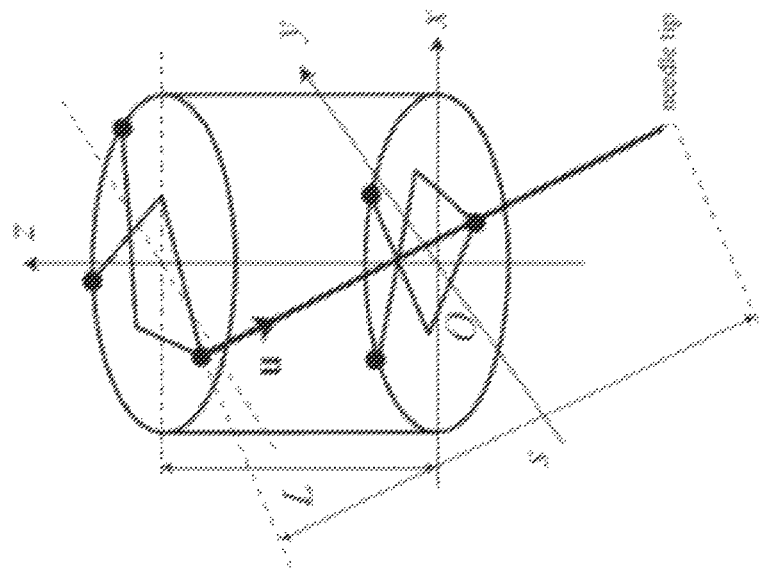
FIG. 4 is a diagram of an example implementation described herein.

FIG. 4 is a diagram of an example implementation 400 described herein. For example, FIG. 4 shows an example schematic diagram of needle tip position of a surgical needle supported by a receptacle of a robot described herein.

As described with regard to FIG. 4, a control device may receive an instruction to move a needle disposed in a receptacle of the robot. The control device may determine a set of commands to move the needle to enable surgical intervention using the needle. Although some implementations are described herein in terms of mathematical calculations to enable movement of the needle, the control device may use another technique, such as a lookup table of positions and/or the like.

Stages of the robot may be located in parallel planes of which the distance between them is denoted as L. For the upper stage, the control device may be configured to determine $p_c^{(t)}$, and for the lower stage, the control device may be configured to determine $p_c^{(b)}$. Then the control device may determine a direction of the needle axis, denoted as the unit vector u, as:

$$u = \frac{P_c^{(b)} - P_c^{(t)}}{\|P_c^{(b)} - P_C^{(t)}\|} \quad (9)$$

where $P_c^{(b)}=[(p_c^{(b)})^T, 0]^T$ and $P_c^{(t)}=[(p_c^{(t)})^T, L]^T$. Based on four angles (two from the upper stage and two from the lower stage), the control device may determine the direction of the needle axis.

Further, the control device may determine a needle tip position inside tissue by including the needle length s. Here, the control device may determine $P_{tip}=[x_{tip}, y_{tip}, z_{tip}]^T$ as the position of the needle tip. Thus, the control device may deter the needle tip position as:

$$P_{tip}=P_c^{(t)}+su \quad (10)$$

In some implementations, the control device may use an inverse kinematics technique determine the four angles of the upper and lower stages, as described above, based on the needle axis and the needle tip position. For example, the control device may determine a line equation from $\{O_{xyz}\}$ system. The control device may parameterize the line equation with four parameters as:

$$\ell(\alpha)=p+\alpha u \quad (11)$$

where $\alpha\in \mathbb{R}$ ($\ell=[\ell_1, \ell_2, \ell_3]^T$). In this case, the control device may determine u (e.g., based on information received from the robot). The control device may have previously determined coordinates of the target point, p, from another reference frame by the measurements. From the other reference frame, the control device also may have determined u. Therefrom, the control device may determine a rigid-body transformation between the measurement frame and the other reference frame that corresponds to the lower stage of the robot. For example, the control device may determine $g=(R, t)$ as the transformation. Further, the control device may determine $P_{tip}^m$ and $u^m$, respectively, as the position of the needle tip and a direction vector from the measurement frame. Then, the control device may determine:

$$P_{tip}=R^T(P_{tip}^m-t), u=R^T u^m. \quad (12)$$

Therefrom, the control device may determine equation (11) by using Eq. (12). As a result, the control device may determine $P_c^{(b)}$ by determining:

$$\ell_3(\alpha)=0 \quad (13)$$

for $\alpha$, then the corresponding $\ell_1$ and $\ell_2$ provide the coordinates of $p_c^{(b)}$. Likewise, the control device may determine:

$$\ell_3(\alpha)=L \quad (14)$$

for $\alpha$, and the corresponding $\ell_1$ and $\ell_2$ give the coordinates of $p_c^{(t)}$ and therefore $p_c^{(t)}$. Then the control device may determine a needle length s as:

$$s=\|P_{tip}-P_c^{(t)}\| \quad (15)$$

Since $p_c^{(t)}$ and $p_c^{(b)}$ are obtained, the control device may only be to determine two angles given $p_c$ in the corresponding plane. Because $\overrightarrow{CM}$ always passes through the origin, $p_c$, which is the position of the point C in the plane, is parallel to n. Also, due the symmetry of the linkage mechanism, the control device may determine:

$$\frac{p_c}{\|p_c\|} = -\begin{pmatrix}\cos\left(\frac{\theta_1+\theta_2}{2}\right)\\ \sin\frac{\theta_1+\theta_2}{2}\end{pmatrix} \quad (16)$$

where the direction of $p_c$ is opposite to $\overrightarrow{CM}$. The control device may determine $v=p_c/p_c=[v_x, v_y]^T(p_c=\|p_c\|)$, and may determine:

$$\theta_1+\theta_2=2(a\tan 2(v_y,v_x)-\pi)=2\varphi \quad (17)$$

where $0\leq\varphi\leq 2\pi$. The control device may modify $a\tan 2(v_y, v_x)$ such that $a\tan 2(v_y, v_x)$ belongs to $[0, 2\pi]$ in order to keep $\varphi\in[0, 2\pi]$. Then, the control device may determine:

$$h = p_c + r\cos\left(\frac{1}{2}(\theta_2-\theta_1)\right) = (d_1+2d_2)\cos\frac{\alpha}{2} \quad (18)$$

by using a set of relationships:

$$\cos\alpha = 1 - \frac{r^2}{d_1^2}(1-\cos(\theta_2-\theta_1)) = 1 - \frac{r^2}{d_1^2}(1-\cos(2\theta_2-2\varphi)), \quad (19)$$

$$1-\cos(2\theta_2-2\varphi)) = 2\sin^2(\theta_2-\varphi)$$

and since $0<\alpha<\pi$, $$\cos\frac{\alpha}{2} = \sqrt{\frac{1+\cos\alpha}{2}},$$

let $\gamma=\theta_2-\varphi$. Then, the control device may determine:

$$p_c + r\cos\gamma = \quad (20)$$

$$(d_1+2d_2)\sqrt{1-\frac{r^2}{d_1^2}\sin^2\gamma} = (d_1+2d_2)\sqrt{1-\frac{r^2}{d_1^2}(1-\cos^2\gamma)}$$

which results in the control device determining:

$$x = \frac{d_1^2 p_c \pm d\sqrt{d_1^2(d_1^2+p_c^2-r^2)+d^2(r^2-d_1^2)}}{r(d^2-d_1^2)} \quad (21)$$

where $x=\cos\gamma(|x|\leq 1)$ and $d=d_1+2d_2$. There are two values of $\gamma$. The control device may select a value, of the two values, by considering a constraint on $\gamma$: $\gamma<\sin^{-1}(d_1/r)$, based on the extreme geometry where the links of the robot are fully folded such that two $d_1$ links are in parallel. By considering this constraint, the control device determines the appropriate sets of angles $\{\theta_1, \theta_2\}$ for the upper and lower stages as $$\theta_2=\varphi+\gamma, \theta_1=\varphi-\gamma \quad (22)$$

As an example of the above, example parameters for the robot geometry are: r=52.25 [mm], $d_1$=20.0 [mm], $d_2$=35.0 [mm] and L=31.0 [mm]. Here, the control device may determine that s=50 [mm].

First, using a forward kinematics technique, the control device may determine $\theta_1$=10°, $\theta_2$=25° for the upper stage, and $\theta_1$=35°, $\theta_2$=58° for the lower stage. Thus, the control device may determine u=[0.3901, −0.2495, −0.8863]$^T$; $P_{tip}$=[−11.7797, −22.3376, −13.3167]$^T$.

Second, using an inverse kinematics technique with the above results, the control device may determine the angles. In this case, the control device may determine that g=(II,0) (e.g., the reference frame for the measurement system is identical with the one attached in the robot (bottom stage)). Thus, the control device may determine $\theta_1$=10.00°, $\theta_2$=25.00° for the upper stage, and $\theta_1$=35°, $\theta_2$=58° for the lower stage. In this way, the control device may mathematically calculate positions and/or angles for controlling the robot. As described above, the control device may use other techniques, such as lookup tables and/or the like, for translating between a desired position for a needle and a corresponding position for portions of the robot to achieve the desired position for the needle.

As indicated above, FIG. 4 is provided merely as an example. Other examples may differ from what was described with regard to FIG. 4.

Figure 5:
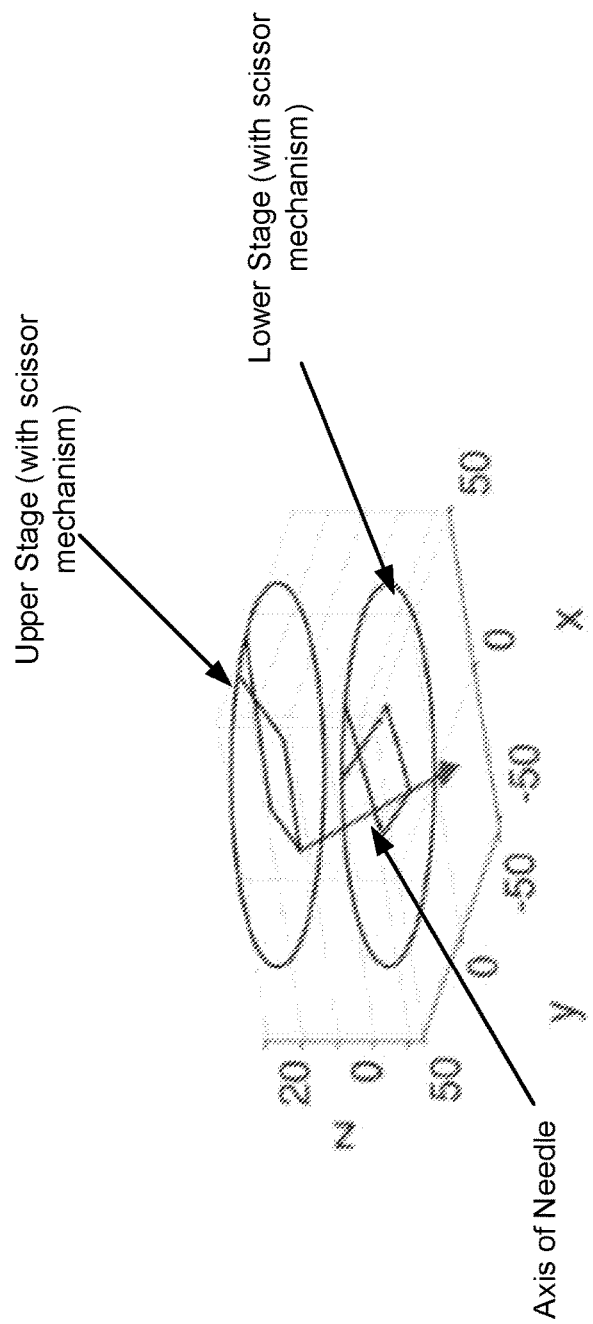
FIG. 5 is a diagram of an example implementation described herein.

FIG. 5 is a diagram of an example implementation 500 described herein. FIG. 5 shows an example of the kinematics of the parallel stages and the needle position. As shown in FIG. 5, based on a position of a scissor mechanism in an upper stage and a position of a scissor mechanism in a lower stage, a particular axis may be achieved for a needle supported by a receptacle at ends of the two scissor mechanisms. In this case, the upper stage and the lower stage provide a 4-DOF of movement of the needle.

As indicated above, FIG. 5 is provided merely as an example. Other examples may differ from what was described with regard to FIG. 5.

Figure 6:
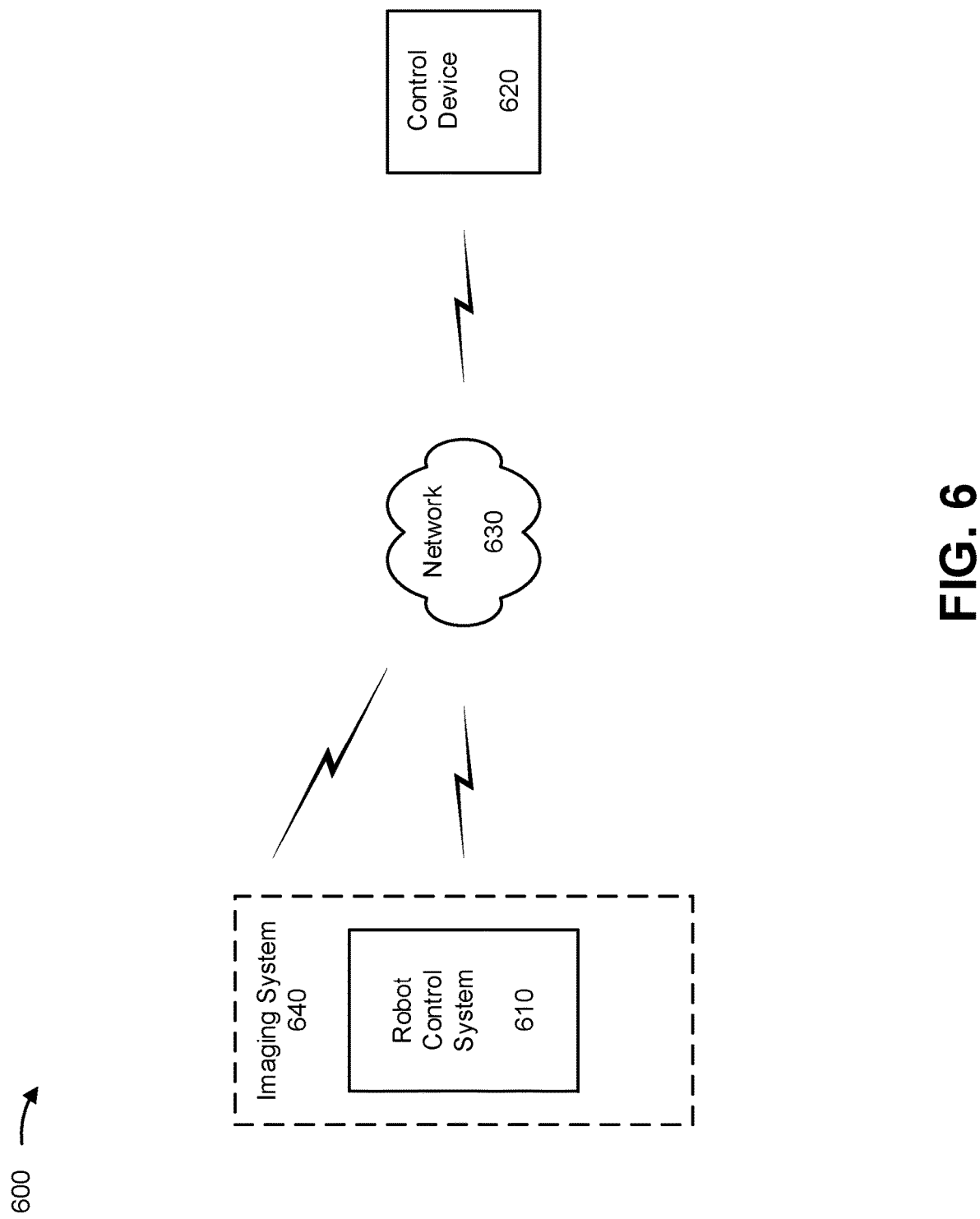
FIG. 6 is a diagram of an example environment in which systems and/or methods, described herein, may be implemented.

FIG. 6 is a diagram of an example environment 600 in which systems and/or methods, described herein, may be implemented. As shown in FIG. 6, environment 600 may include a robot control system 610, a control device 620, a network 630, and an imaging system 640. Devices of environment 600 may interconnect via wired connections, wireless connections, or a combination of wired and wireless connections.

Robot control system 610 includes one or more devices capable of receiving, generating, storing, processing, and/or providing information associated with controlling a robot. For example, robot control system 610 may receive instructions from control device 620 to move a needle guide, which may receive a needle, being held by the robot, and may actuate one or more actuators of the robot to move the needle guide. In some implementations, the needle may be automatically inserted. In some implementations, the needle may be inserted into the needle guide by an operator based on the needle guide being moved to a selected orientation and location, and based on providing an indication that the needle guide is at the selected orientation and location. In some implementations, robot control system 610 and an associated body mountable robot may be disposed inside imaging system 640 to enable concurrent surgical intervention and imaging (e.g., imaging assisted surgical intervention). In some implementations, robot control system 610 may connect to control device 620 via encoder cables, motor cables, and/or the like.

Control device 620 includes one or more devices capable of receiving, generating, storing, processing, and/or providing information associated with controlling a robot. For example, control device 620 may determine to move a needle being held by a robot, may determine a set of commands to cause the needle to be moved, and may transmit the set of commands to robot control system 610 to cause the needle to be moved. In some implementations, control device 620 includes a user device, such as a mobile phone (e.g., a smart phone, a radiotelephone, etc.), a laptop computer, a tablet computer, a handheld computer, a gaming device, a wearable communication device (e.g., a smart wristwatch, a pair of smart eyeglasses, etc.), and/or a similar type of device. In some implementations, control device 620 provides a user interface and one or more input peripherals (e.g., a joystick) to receive commands from a technician. In some implementations, control device 620 may communicate with a magnetic resonance imaging (MRI) machine to receive imaging associated with a robot, may automatically determine a movement for a needle held by the robot based on the imaging, and may automatically provide a command to effectuate the movement. In some implementations, control device 620 may include a robot control workstation, an MRI host workstation, a planning workstation, a real-time MRI screen, and/or the like.

Network 630 includes one or more wired and/or wireless networks. For example, network 630 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

Imaging system 640 includes one or more devices capable of receiving, generating, storing, processing, and/or providing information associated with imaging. For example, imaging system 640 may include an MRI device that may capture imaging of a patient. In some implementations, imaging system 640 may provide output identifying the imaging to control device 620 for display. In some implementations, imaging system 640 may provide output identifying the imaging to control device 620 to enable control device 620 to perform object recognition and automatically control robot control system 610 based on the object recognition.

The number and arrangement of devices and networks shown in FIG. 6 are provided as an example. In practice, there may be additional devices and/or networks, fewer devices and/or networks, different devices and/or networks, or differently arranged devices and/or networks than those shown in FIG. 6. Furthermore, two or more devices shown in FIG. 6 may be implemented within a single device, or a single device shown in FIG. 6 may be implemented as multiple, distributed devices. Additionally, or alternatively, a set of devices (e.g., one or more devices) of environment 600 may perform one or more functions described as being performed by another set of devices of environment 600.

Figure 7:
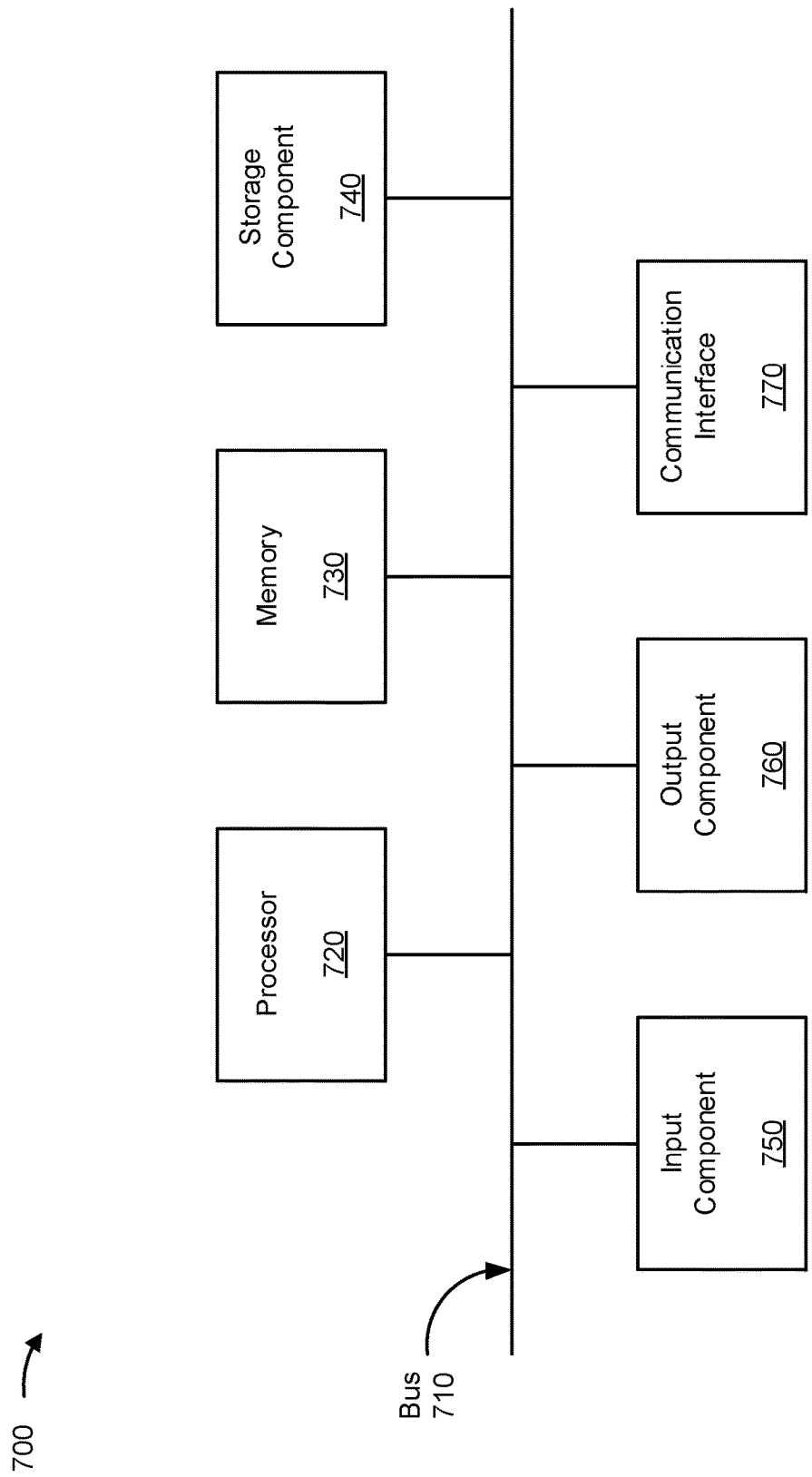
FIG. 7 is a diagram of example components of one or more devices of FIG. 6.

FIG. 7 is a diagram of example components of a device 700. Device 700 may correspond to robot control system 610, control device 620, and/or imaging system 640. In some implementations, robot control system 610, control device 620, and/or imaging system 640 may include one or more devices 700 and/or one or more components of device 700. As shown in FIG. 7, device 700 may include a bus 710, a processor 720, a memory 730, a storage component 740, an input component 750, an output component 760, and a communication interface 770.

Bus 710 includes a component that permits communication among the components of device 700. Processor 720 is implemented in hardware, firmware, or a combination of hardware and software. Processor 720 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 720 includes one or more processors capable of being programmed to perform a function. Memory 730 includes a random-access memory (RAM), a read only memory (ROM), and/or another type of dynamic or static storage device (e.g., a flash memory, a magnetic memory, and/or an optical memory) that stores information and/or instructions for use by processor 720.

Storage component 740 stores information and/or software related to the operation and use of device 700. For example, storage component 740 may include a hard disk (e.g., a magnetic disk, an optical disk, a magneto-optic disk, and/or a solid-state disk), a compact disc (CD), a digital versatile disc (DVD), a floppy disk, a cartridge, a magnetic tape, and/or another type of non-transitory computer-readable medium, along with a corresponding drive.

Input component 750 includes a component that permits device 700 to receive information, such as via user input (e.g., a touch screen display, a keyboard, a keypad, a mouse, a button, a switch, and/or a microphone). Additionally, or alternatively, input component 750 may include a sensor for sensing information (e.g., a global positioning system (GPS) component, an accelerometer, a gyroscope, and/or an actuator). Output component 760 includes a component that provides output information from device 700 (e.g., a display, a speaker, and/or one or more light-emitting diodes (LEDs)).

Communication interface 770 includes a transceiver-like component (e.g., a transceiver and/or a separate receiver and transmitter) that enables device 700 to communicate with other devices, such as via a wired connection, a wireless connection, or a combination of wired and wireless connections. Communication interface 770 may permit device 700 to receive information from another device and/or provide information to another device. For example, communication interface 770 may include an Ethernet interface, an optical interface, a coaxial interface, an infrared interface, a radio frequency (RF) interface, a universal serial bus (USB) interface, a Wi-Fi interface, a cellular network interface, or the like.

Device 700 may perform one or more processes described herein. Device 700 may perform these processes based on processor 720 executing software instructions stored by a non-transitory computer-readable medium, such as memory 730 and/or storage component 740. A computer-readable medium is defined herein as a non-transitory memory device. A memory device includes memory space within a single physical storage device or memory space spread across multiple physical storage devices.

Software instructions may be read into memory 730 and/or storage component 740 from another computer-readable medium or from another device via communication interface 770. When executed, software instructions stored in memory 730 and/or storage component 740 may cause processor 720 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 7 are provided as an example. In practice, device 700 may include additional components, fewer components, different components, or differently arranged components than those shown in FIG. 7. Additionally, or alternatively, a set of components (e.g., one or more components) of device 700 may perform one or more functions described as being performed by another set of components of device 700.

Figure 8:
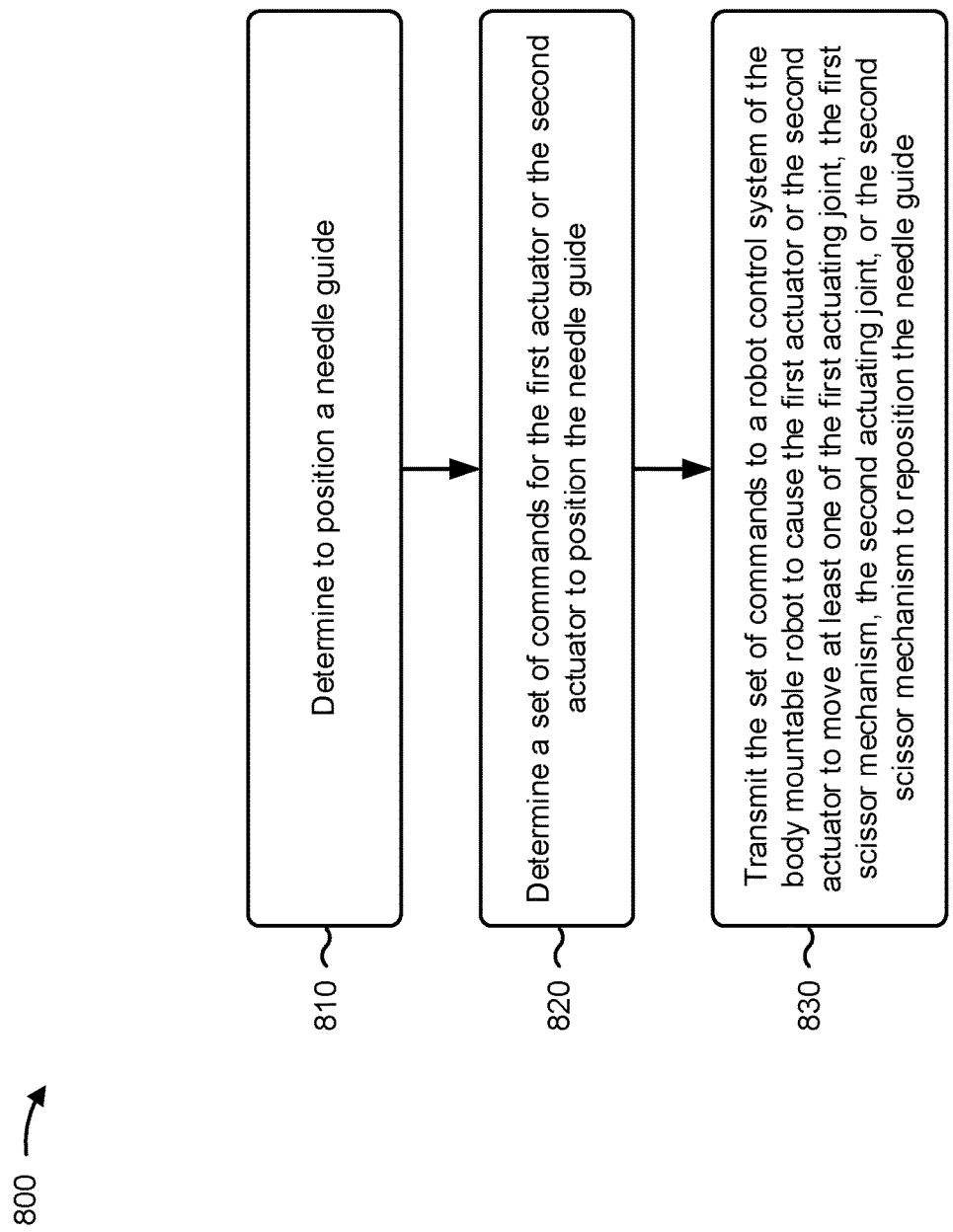
FIG. 8 is a flow chart of an example process for controlling a body mountable robot.

FIG. 8 is a flow chart of an example process 800 for controlling a body mountable robot. In some implementations, one or more process blocks of FIG. 8 may be performed by a control device (e.g., control device 620). In some implementations, one or more process blocks of Fig. F2 may be performed by another device or a group of devices separate from or including the a control device (e.g., control device 620), such as a robot control system (e.g., robot control system 610), and/or the like.

As shown in FIG. 8, process 800 may include determining to position a needle guide (block 810). For example, the control device (e.g., using processor 720, memory 730, storage component 740, and/or the like) may determine to position a needle guide, as described above. In some implementations, the needle guide is supported by an upper stage and a lower stage of a body mountable robot. In some implementations, the upper stage includes a first actuating joint to move about the upper stage, a first actuator to move the first actuating joint, and a first scissor mechanism to move about the upper stage. In some implementations, the lower stage includes a second actuating joint to move about the lower stage, a second actuator to move the second actuating joint, and a second scissor mechanism to move about the lower stage.

As further shown in FIG. 8, process 800 may include determining a set of commands for the first actuator or the second actuator to position the needle guide (block 820). For example, the control device (e.g., using processor 720, memory 730, storage component 740, and/or the like) may determine a set of commands for the first actuator or the second actuator to position the needle guide, as described above.

As further shown in FIG. 8, process 800 may include transmitting the set of commands to a robot control system of the body mountable robot to cause the first actuator or the second actuator to move at least one of the first actuating joint, the first scissor mechanism, the second actuating joint, or the second scissor mechanism to reposition the needle guide (block 830). For example, the control device (e.g., using processor 720, output component 760, communication interface 770, and/or the like) may transmit the set of commands to a robot control system of the body mountable robot to cause the first actuator or the second actuator to move at least one of the first actuating joint, the first scissor mechanism, the second actuating joint, or the second scissor mechanism to reposition the needle guide, as described above.

Process 800 may include additional implementations, such as any single implementation or any combination of implementations described below and/or in connection with one or more other processes described elsewhere herein.

In some implementations, the control device may receive input indicating that the needle guide is to be moved from a first location to a second location. In some implementations, the first actuator is a first piezoelectric motor and the second actuator is a second piezoelectric motor. In some implementations, the control device may receive magnetic resonance imaging of a patient, determine, based on the magnetic resonance imaging, an initial position of the needle guide, determine, based on the magnetic resonance imaging, a target position of the needle guide, and determine to move the needle guide from the initial position to the target position.

Additionally, or alternatively, a body mountable robot may include a set of stages disposed in a parallel configuration; a set of actuating joints, wherein an actuating joint, of the set of actuating joints, is configured to rotate with respect to a corresponding stage of the set of stages; at least one actuator, wherein the at least one actuator is configured to actuate at least one actuating joint of the set of actuating joints; and a set of scissor mechanisms, wherein a scissor mechanism, of the set of scissor mechanisms, that is coupled to the actuating joint, is supported by the corresponding stage, and wherein the scissor mechanism is configured to translate with respect to the corresponding stage.

Such a body mountable robot may include additional implementations, such as any single implementation or any combination of implementations described below and/or in connection with one or more other processes described elsewhere herein.

In some implementations, the scissor mechanism, the actuating joint, and the corresponding stage combine to provide two degrees of freedom of motion for a receptacle supported by the scissor mechanism, the actuating joint, and the corresponding stage. In some implementations, another scissor mechanism, of the set of scissor mechanisms, another actuating joint, of the set of actuating joints, and another stage, of the set of stages, combine to provide another two degrees of freedom for the receptacle, such that the receptacle has four degrees of freedom of motion. In some implementations, the receptacle supports a needle guide. In some implementations, the needle guide is rotatable by an angular range of between −30 degrees and 30 degrees of an initial position. In some implementations, the body mountable robot may include an optical encoder to provide feedback information identifying a motion of at least one of: the at least one actuator, the set of actuating joints, the set of stages, or the set of scissor mechanisms.

In some implementations, the body mountable robot may include a robot control system to control at least one of: the at least one actuator, the set of actuating joints, the set of stages, or the set of scissor mechanisms. In some implementations, components of the body mountable robot are composed of a magnetic resonance imaging (MRI)-compatible material. In some implementations, the body mountable robot may include a base to support at least one of the at least one actuator, the set of actuating joints, the set of stages, or the set of scissor mechanisms. In some implementations, the base is configured to be securely mounted to a portion of a human body. In some implementations, the body mountable robot may include an integrated magnetic resonance imaging (MRI) coil to perform MRI imaging. In some implementations, the base is configured to mount to a shoulder of a patient.

Additionally, or alternatively, a system may include the body mountable robot, wherein the body mountable robot is configured for use within an MRI machine and includes a set of stages disposed in a parallel configuration, a set of actuating joints, at least one actuator, a set of scissor mechanisms, a needle guide, and a robot control system to control the body mountable robot to move the needle guide with regard to four degrees of freedom of movement, and the system may include a control device to transmit control signals to the robot control system based on imaging information from the MRI machine.

Such a system may include additional implementations, such as any single implementation or any combination of implementations described below and/or in connection with one or more other processes described elsewhere herein.

In some implementations, a scissor mechanism, of the set of scissor mechanisms, includes a plurality of connected link bars, and the plurality of connected link bars are connected by at least one spherical joint. In some implementations, the body mountable robot further comprises a base, the at least one actuator is connected to the base, and at least one power or data cable is connected to the at least one actuator at the base. In some implementations, the control device is configured to transmit the control signals to guide a percutaneous intervention. In some implementations, the percutaneous intervention is an arthrography procedure.

Although FIG. 8 shows example blocks of process 800, in some implementations, process 800 may include additional blocks, fewer blocks, different blocks, or differently arranged blocks than those depicted in FIG. 8. Additionally, or alternatively, two or more of the blocks of process 800 may be performed in parallel.

The foregoing disclosure provides illustration and description, but is not intended to be exhaustive or to limit the implementations to the precise form disclosed. Modifications and variations may be made in light of the above disclosure or may be acquired from practice of the implementations.

As used herein, the term "component" is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, or the like.

Certain user interfaces have been described herein and/or shown in the figures. A user interface may include a graphical user interface, a non-graphical user interface, a text-based user interface, or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A system, comprising:
   a body mountable robot configured for use within a magnetic resonance imaging (MRI) machine, comprising:
      a plurality of stages, disposed in a parallel configuration, comprising:
         a first stage including a first actuating joint configured to rotate about a vertical axis with respect to the first stage, and
         a second stage including a second actuating joint configured to rotate about the vertical axis with respect to the second stage;
      at least one actuator configured to actuate at least one of the first actuating joint or the second actuating joint, and
      a plurality of sets of link bars, comprising:
         a first set of link bars, coupled to the first actuating joint, configured to translate with respect to the first stage, and
         a second set of link bars, coupled to the second actuating joint, configured to translate with respect to the second stage; and
   a control device configured to transmit control signals to the body mountable robot based on imaging information from the MRI machine.

2. The system of claim 1, wherein the plurality of sets of link bars are connected by at least one spherical joint.

3. The system of claim 1, wherein the body mountable robot further comprises a base,
   wherein the at least one actuator is connected to the base, and
   wherein at least one power or data cable is connected to the at least one actuator at the base.

4. The system of claim 1, wherein the at least one actuator comprises a first actuator configured to actuate the first actuating joint and a second actuator configured to actuate the second actuating joint.

5. The system of claim 1, further comprising:
   a first pair of piezoelectric motors corresponding to the first actuating joint, and
   a second pair of piezoelectric motors corresponding to the second actuating joint.

6. The system of claim 1, wherein the control device is configured to transmit the control signals to guide a percutaneous intervention.

7. The system of claim 6, wherein the percutaneous intervention is an arthrography procedure.

8. A system, comprising:
   a control device to:
      determine a set of commands to cause a receptacle to be moved, and transmit the set of commands; and
   a robot control system to:
      receive the set of commands, and
      actuate, based on the set of commands at least one of
         a plurality of actuating joints of a plurality of stages in a parallel configuration,
         wherein the plurality of actuating joints comprises:
            a first actuating joint coupled to a first set of link bars, wherein the first actuating joint is configured to rotate about a vertical axis with respect to a first stage of the plurality of stages, and
            wherein the first set of link bars are configured to translate with respect to the first stage, and a second actuating joint coupled to a second set of link bars, wherein the second actuating joint is configured to rotate about the vertical axis with respect to a second stage of the plurality of stages, and wherein the second set of link bars are configured to translate with respect to the second stage.

9. The system of claim 8, wherein the robot control system is further to:
provide feedback information identifying a motion of at least one of: the plurality of actuating joints, the first set of link bars, the second set of link bars, or the plurality of stages.

10. The system of claim 8, wherein the receptacle supports a needle guide.

11. The system of claim 10, wherein the needle guide is rotatable.

12. The system of claim 8, wherein the first stage, the first actuating joint, and the first set of link bars combine to provide at least two degrees of freedom of motion for the receptacle.

13. The system of claim 12, wherein the second stage, the second actuating joint, and the second set of link bars combine to provide at four degrees of freedom of motion for the receptacle.

14. A system, comprising:
a robot to:
receive a set of commands to move a receptacle for a needle, and
actuate, based on the set of commands, at least one of a plurality of actuating joints of a plurality of stages in a parallel configuration,
wherein the plurality of actuating joints comprises:
a first actuating joint coupled to a first set of link bars, wherein the first actuating joint is configured to rotate about a vertical axis with respect to a first stage of the plurality of stages, and wherein the first set of link bars are configured to translate with respect to the first stage, and
a second actuating joint coupled to a second set of link bars, wherein the second actuating joint is configured to rotate about the vertical axis with respect to a second stage of the plurality of stages, and wherein the second set of link bars are configured to translate with respect to the second stage.

15. The system of claim 14, wherein the system is a robot control system.

16. The system of claim 14, wherein the plurality of stages are a plurality of circular stages.

17. The system of claim 14, wherein the first stage comprises a first set of discs connected to the first set of link bars, and wherein the second stage comprises a second set of discs connected to the second set of link bars.

18. The system of claim 14, wherein the first set of link bars are connected by a first set of spherical joints through which the receptacle passes, and wherein the second set of link bars are connected by a second set of spherical joints through which the receptacle passes.

19. The system of claim 14, wherein the robot is further to:
determine a movement of the at least one of the plurality of actuating joints to actuate the at least one of the plurality of actuating joints.

20. The system of claim 19, wherein the movement of the at least one of the plurality of actuating joints includes an angle of the at least one of the plurality of actuating joints.

\* \* \* \* \*